US 8,574,830 B2

(12) United States Patent
Mookkan et al.

(10) Patent No.: US 8,574,830 B2
(45) Date of Patent: Nov. 5, 2013

(54) BINDING PROTEIN AND EPITOPE-BLOCKING ELISA FOR THE UNIVERSAL DETECTION OF H5-SUBTYPE INFLUENZA VIRUSES

(75) Inventors: Prabakaran Mookkan, Singapore (SG); Nayana Prabhu Padubidhri, Singapore (SG); Sumathy Velumani, Singapore (SG); Hwei-Sing Jimmy Kwang, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 396 days.

(21) Appl. No.: 12/865,543

(22) PCT Filed: Feb. 5, 2008

(86) PCT No.: PCT/SG2008/000043
§ 371 (c)(1),
(2), (4) Date: Oct. 26, 2010

(87) PCT Pub. No.: WO2009/099394
PCT Pub. Date: Aug. 13, 2009

(65) Prior Publication Data
US 2011/0053142 A1    Mar. 3, 2011

(51) Int. Cl.
*C12Q 1/70*    (2006.01)
*C07K 16/10*    (2006.01)

(52) U.S. Cl.
USPC ...... 435/5; 530/387.9; 530/388.3; 530/389.4; 435/7.1

(58) Field of Classification Search
None
See application file for complete search history.

(56) References Cited

FOREIGN PATENT DOCUMENTS

| EP | 1820511 A1 | 8/2007 |
|---|---|---|
| WO | 2007021002 A1 | 2/2007 |
| WO | 2007074812 A1 | 7/2007 |
| WO | 2007/089753 A2 | 8/2007 |

OTHER PUBLICATIONS

Hemagglutinin [Influenza A virus (A/Indonesia/CDC669/2006(H5N1))] GenBank: ABI36428.1—dated 2006.*
Philpott et al., J Virology 1989 vol. 63, pp. 3453-3458 abstract only.*
Green et al., J of Infectious Diseases 1990 vol. 161, pp. 667-679 abstract only.*
Boen, Eric, "Identification of T Cell Ligands in a Library of Peptides Covalently Attached to HLA-DR4," Journal of Immunology, 165: 2040-2047 (2000).
Kaverin, N, et al., "Epitope Mapping of the Hemagglutinin Molecule of a Highly Pathogenic H5N1 Influenza Virus by Using Monoclonal Antibodies," Journal of Virology, 81(23): 12911-12917 (Dec. 2007).
Somvanshi, Pallavi, et al., "Prediction of Epitopes in Hemagglutinin and Neuraminidase Proteins of Influenza A Virus H5N1 Strain: A Clue for Diagnostic and Vaccine Development," A Journal of Integrative Biology, 12(1): 61-69 (2008).
Luo, H.F. et al., "Characterization of a broad-spectrum neutralization monoclonal antibody against haemagglutinin of H5 subtype avian influenza virus," Bingdu Xuebao—Chinese Journal of Virology, Zhongguo Weishengwu Xuchui, Beijing, CN, vol. 23, No. 2, Mar. 1, 2007, pp. 85-90, XP001525197. English abstract.
Prabakaran, M. et al., "Development of epitope-blocking ELISA for universal detection of anibodies to human H5N1 influenza viruses," PLOS ONE, vol. 4, No. 2, Feb. 2009, XP002679106.
Velumani, S. et al., "A novel peptide ELISA for universal detection of antibodies to human H5N1 influenza viruses," PLOS ONE, vol. 6, No. 6, Jun. 2011, XP002678179.
Extended EP Search Report, Ref No. HB/P42280EP, Application No. 08712870.8-2406 /2250197 PCT/SG2008000043, Applicant: Temasek Life Sciences Laboratory Limited, 12 pages.
Japanese Office Action, Notification of Reason for Rejection, JP Application No. 2010-545833, Date of Delivery: Nov. 30, 2012, Examiner: Kozue Ogura (4504 4B00), 6 pages.
He, Q. et al., "Detection of H5 Avian Influenza Viruses by Antigen-Capture Enzyme-Linked Immunosorbent Assay Using H5-Specific Monoclonal Antibody," Clinical and Vaccine Immunology, May 2007, vol. 14, No. 5, pp. 617-623, © 2007 American Society for Microbiology.

* cited by examiner

*Primary Examiner* — Mary E Mosher
*Assistant Examiner* — Myron Hill
(74) *Attorney, Agent, or Firm* — Rothwell, Figg, Ernst & Manbeck P.C.

(57) ABSTRACT

Monoclonal antibodies and related binding proteins specific to influenza H5 subtype HA protein can be used in serological diagnosis of influenza H5 infection in mammalian and avian serum samples, including human serum samples. Each antibody reacts strongly with a wide variety of strains of H5 subtype and does not show cross-reactivity with non-H5 influenza subtypes.

15 Claims, 12 Drawing Sheets

58 kDa

Figure 2B
C  A  B  C  D  E
39 kDa ▬
Figure 2C
SF1 SF2 SF3 SF4 SF5 SF6 SF7 SF8
Fig: 2D
1  2  3  4  5  6  7  8  9  10  11  12  13  14  15

| AA1 | | | | | | | AA337 |
|---|---|---|---|---|---|---|---|
| AA1 | (a) | AA75 | | | | | |
| | AA61 | (b) | AA135 | | | | |
| | | AA121 | (c) | AA195 | | | |
| | | | AA181 | (d) | AA255 | | |
| | | | | AA241 | (e) | AA337 | |

| AA181 | (d) | | AA255 | |
|---|---|---|---|---|
| | AA241 | (e) | | AA337 |
| AA181 | (SF1) | AA270 | | |
| AA181 | (SF2) | AA280 | | |
| AA181 | (SF3) | AA290 | | |
| AA181 | (SF4) | | AA300 | |
| AA181 | (SF5) | | AA310 | |
| AA181 | (SF6) | | AA320 | |
| AA181 | (SF7) | | AA330 | |
| AA181 | (SF8) | | | AA337 |

Results of western blotting

|  | Amino acid number: | Result on Western blot-1G5 |
|---|---|---|
| rHA1 | 1-337 | + |
| Fragment A | 1-75 | - |
| Fragment B | 61-135 | - |
| Fragment C | 121-195 | - |
| Fragment D | 181-255 | - |
| Fragment E | 241

SF1 SF2 SF3 SF4 SF5 SF6 SF7 SF8

Fig 5D: Western blot analysis of the point mutated fragments.

SEQUENCE LISTING

<160> NUMBER OF SEQ ID NOS: 6

<210> SEQ ID NO 1
<211> LENGTH: 8
<212> TYPE: PRT
<213> ORGANISM: Avian influenza virus

```
<400> SEQUENCE: 1

Cys Asn Thr Lys Cys Gln Thr Pro
1               5

<210> SEQ ID NO 2
<211> LENGTH: 8
<212> TYPE: PRT
<213> ORGANISM: Avian influenza virus

<400> SEQUENCE: 2

Ile His Pro Leu Thr Ile Gly Glu
1               5

<210> SEQ ID NO 3
<211> LENGTH: 8
<212> TYPE: PRT
<213> ORGANISM: Avian influenza virus

<400> SEQUENCE: 3

Cys Asn Thr Arg Cys Gln Thr Pro
1               5

<210> SEQ ID NO 4
<211> LENGTH: 8
<212> TYPE: PRT
<213> ORGANISM: Avian influenza virus

<400> SEQUENCE: 4

Cys Asn Thr Lys Cys Gln Thr Leu
1               5

<210> SEQ ID NO 5
<211> LENGTH: 8
<212> TYPE: PRT
<213> ORGANISM: Avian influenza virus

<400> SEQUENCE: 5

Cys Asn Ala Lys Cys Gln Thr Pro
1               5

<210> SEQ ID NO 6
<211> LENGTH: 13
<212> TYPE: PRT
<213> ORGANISM: Avian influenza virus

<400> SEQUENCE: 6

His Asn Ile His Pro Leu Thr Ile Gly Glu Cys Pro Lys
1               5                   10
```

BINDING PROTEIN AND EPITOPE-BLOCKING ELISA FOR THE UNIVERSAL DETECTION OF H5-SUBTYPE INFLUENZA VIRUSES

This application is a national filing under 35 USC §371 of PCT/SG2008/000043, filed Feb. 5, 2008. The prior application is incorporated herein.

SEQUENCE SUBMISSION

The present application includes a Sequence Listing filed in electronic format. The Sequence Listing is entitled 2577185SequenceListing.txt, was created on 8 Jan. 2013 and is 2 kb in size. The information in the electronic format of the Sequence Listing is part of the present application and is incorporated herein by reference in its entirety.

FIELD OF THE INVENTION

This invention relates to the development of a specific serological assay for the detection of antibodies to avian influenza viruses. More specifically, this invention relates to the production of monoclonal antibodies which react strongly with all known subtypes of H5 influenza virus, but which do not cross-react with non-H5 influenza subtypes, and are used to develop epitope blocking ELISAs to detect serum antibody and related binding protein to H5 influenza subtype in humans and non-human animals.

DESCRIPTION OF THE BACKGROUND ART

Avian influenza virus (AIV) is a common disease in birds. The first infection of subtype H5N1 AIV among poultry was detected in 1996 in a farmed goose in Guangdong Province, China, and in humans a year later in Hong Kong [1]. Since then, H5N1 AIV has caused an outbreak of avian influenza that is spreading to many regions of the world. The affected areas to date include Europe, the Middle East and, particularly, Asia [2]. According to the latest reports from the World Health Organization (WHO), there have been a total of 328 confirmed human H5N1 avian influenza cases, 200 of which resulted in the death of the patient. Of the 328 cases, a significant majority (106 cases, 85 deaths) have been reported from Indonesia [3,4]. According to WHO, the world now is in phase 3 (of 6) of a pandemic alert based upon the evolution of the virus into a strain that is capable of efficient human to human transmission [5].

In June, 2006, 27 of 33 provinces in Indonesia had reported outbreaks of H5N1 in poultry, resulting in more than 16 million poultry deaths from sickness and culling [6]. The poultry industry has lost millions of dollars to avian influenza. This loss has affected the incomes of millions of people whose livelihoods depend on poultry. These outbreaks of HPAI (H5N1) in poultry, and now the increasing number of cases in humans, are a cause for concern. The ability to accurately and timely detect the presence of the pathogen in the initial stages of an outbreak will go a long way in controlling the disease. In addition, it can reduce indiscriminate use of antibiotics and provide the option of using antiviral therapy in a timely manner.

Various methods available for the diagnosis of influenza include virus isolation, detection of viral antigens by enzyme-linked immunoabsorbent assay (ELISA), molecular detection by RT-PCR and serological tests. Standard virus-isolation procedures have the disadvantage of requiring several days to obtain results, thereby making them of limited use to a clinician. The disadvantages of RT-PCR include the high costs involved, the need for technically proficient staff, likelihood of contamination and the consequent risk of false positive results. In addition, PCR primers may require constant updating because of antigenic drift [7]. Virus neutralization, hemagglutination inhibition (HI), ELISA and immunoblot test are preferred methods for serological diagnosis. However, neutralization assay and HI assay are not considered highly sensitive and necessitate further sub-typing and also are quite labor-intensive and time-consuming [8,9] and so are not ideal for large-scale routine testing of sera. ELISA has been widely used as a pre-screening tool for investigating large numbers of samples, but indirect ELISA systems are commercially available only for chicken and turkey sera due to the unavailability of species-specific secondary antibodies of other species. A further limitation of indirect ELISA is the need for high antigen purity. The most significant disadvantage of the indirect ELISA, however, is that the HA antigen is known to cross-react with the other subtypes of viruses. As a consequence, the indirect ELISA is not a dependable method for detection.

Most of these methods not only are cumbersome and labor intensive but also are time-consuming and include a risk of obtaining false positive results. A further limitation of these techniques is that influenza viruses are segmented genome RNA viruses which are known to undergo continuous mutations and genetic re-assortments (antigenic drift), making it difficult to detect the virus [10].

In view of the shortcomings of these conventional assays, and because of the risk that AIV infection poses to wildlife, domesticated animals and humans, there is a high need for a new assay which is rapid, easy to use and specific for the detection of the H5 subtype of AIV. The present invention represents a breakthrough in the diagnosis and surveillance of H5 subtype of AIV.

SUMMARY OF THE INVENTION

In accordance with the present invention, monoclonal antibodies and related binding proteins specific to influenza H5 subtype HA protein are provided. The antibodies can be used in serological diagnosis of influenza H5 infection in mammalian and avian serum samples, including human serum samples. More specifically, each antibody can be used in a highly sensitive and specific epitope-blocking ELISA to detect influenza H5 subtypes in humans and other animals. Each antibody strongly reacts with a wide variety of strains of H5 subtype and does not show cross-reactivity with non-H5 influenza subtypes.

Accordingly, the invention comprises a binding protein that binds to an epitope of an H5 subtype of avian influenza virus having substantially the immunological binding characteristics of monoclonal antibody 5F8 or monoclonal antibody 1G5. The binding protein can be a monoclonal antibody, antibody fragment, chimeric antibody or humanized antibody and preferably is a monoclonal antibody.

The invention further comprises a binding protein which binds to an epitope of AIV H5 hemagglutinin of amino acid sequence CNTKCQTP (SEQ ID NO:1). The invention also comprises a binding protein which binds to an epitope of AIV H5 hemagglutinin of amino acid sequence IHPLTIGE (SEQ ID NO:2).

In a further aspect, the invention comprises a method for detecting H5 subtype AIV in a biological specimen which comprises contacting the specimen with an antigen which contains an epitope of an H5 subtype hemagglutinin glycoprotein and determining whether an antibody in the specimen binds to the epitope. Preferably the binding determination is made in an epitope blocking ELISA. Preferably the epitope of the H5 subtype hemagglutinin glycoprotein includes the sequence CNTKCQTP (SEQ ID NO:1) or the sequence IHPLTIGE (SEQ ID NO:2). Both the IHPLTIGE (SEQ ID NO:2) and the CNTKCQTP (SEQ ID NO:1) epitopes exist in all known human H5N1 AIV strains, in essentially all known chicken H5N1 AIV strains, and in essentially all known H5N1 strains of other animals and birds, and are very stable and highly antigenic, making them very useful for diagnosing H5N1 infections.

The invention further is directed to a kit for detecting H5 subtype AIV infection in a biological specimen, wherein the kit comprises a binding protein that binds to an epitope of the envelope glycoprotein of an H5 subtype AIV, together with reagents for detecting binding of the binding protein to the epitope. In a preferred embodiment, the epitope includes the sequence CNTKCQTP (SEQ ID NO:1). In another preferred embodiment, the epitope includes the sequence IHPLTIGE (SEQ ID NO:2). In a preferred embodiment, the binding protein has substantially the immunological binding characteristics of mAb 5F8. In another preferred embodiment, the binding protein has substantially the immunological binding characteristics of mAb 1G5.

BRIEF DESCRIPTION OF THE DRAWINGS

FIGS. 1A 1-4 show the recognition of native HA1 in H5N1 AIV-infected MDCK cells and baculovirus expressed rHA1 by mAb 5F8 in immunofluorescence assay. The MDCK and Sf-9 cells were infected with H5 subtypes and recombinant baculoviruses, respectively. The control was H9N2-infected MDCK cells and Sf-9 cells.

FIG. 1B shows the recognition of H5N1 AIV by MAb 5F8 in Western blot. The purified AIV H5N1 (lanes 1-9), H5N2 (lane 10) and H5N3 (lane 11) from allantoic fluid were analyzed by SDS-PAGE and immobilized onto nitrocellulose membrane. The negative control (no virus), H3N2 (lane 12), H7N1 (lane 13) HA were not recognized by MAb 5F8, which shows the specificity of the antibodies to H5 subtypes.

FIGS. 2A, 2B, 2C and 2D. Epitope mapping of the MAb 5F8.

FIG. 2A shows the strategy used for the epitope mapping. All of the indicated fragments from A to E and SF1 to SF8 were expressed as His-fusion proteins. Western blot analysis shown in FIG. 2B of fragments A to E used MAb 5F8 as the primary antibody. C:rHA1 protein was used as control. FIG. 2C shows the results of Western blot analysis of eight further truncated peptides (SF1-SF8) which were an extension of fragment 4 of FIG. 2A but truncated in the fragment 5 region and expressed as histidine-fusion peptides. FIG. 2D shows the results of a Western blot analysis of point mutants also expressed as histidine-fusion peptides. The analysis was carried out to determine the amino acid sequence of the epitope for mAb 5F8.

FIGS. 3A and 3B show the 50% blocking of mAb binding relative to the CDC/523/H5HA1 epitope or rH5HA1 caused by immunized chicken sera. The results were expressed as the arithmetic mean of percent blocking value (n=5/group+standard error (SE)).

FIGS. 4A 1-4 show that mAb 1G5 recognizes native HA in H5N1 AIV-infected MDCK cells and Sf-9 infected baculovirus in immunofluorescence assay. The MDCK and Sf-9 cells were infected with H5 virus or recombinant H5HA baculovirus, respectively. The control was H4N1-infected MDCK cells and Sf-9 cells.

FIG. 4B shows the recognition of H5HA by mAb 1G5 in Western blot. The monoclonal antibody recognized H5HA in each of lanes 1-14. Non-H5 virus in lane 15 was not recognized by 1G5, showing the antibody's specificity to H5 subtypes.

FIGS. 5A-5D. Epitope mapping of mAb 1G5. FIG. 5A shows the strategy used for the epitope mapping. All of the indicated fragments from A to E and SF1 to SF8 were expressed as His-fusion fragments as in Example 1. Western blot analysis shown in FIG. 5B of fragments A to E used mAb 1G5 as the primary antibody. C:rHA1 protein was used as control. Western blot analyses of subfragments SF1 to SF8 and of the point mutants of the final step of the epitope determination are shown in FIGS. 5C and 5D, respectively.

FIG. 6A shows that the antibodies reacted specifically with 15 different samples of Indonesian H5N1 strains; FIG. 6B shows the antibodies reacted specifically with Indonesian H5N1 strains (1-9), H5N1/PR8 (10); H5N2 (11) and H5N3 (12), but not H4N1 or H7N1 (13 and 14, respectively). Assays were performed using mAb 5F8, 1G5 or a combination thereof as capture antibodies and polyclonal anti-H5HA1 as the detector antibody.

In FIG. 9A, samples 1-14 were H5N1 Indonesian strains immunized chicken serum samples at a 1:30 dilution. In FIG. 9B, samples 1-10 were H5N1 Indonesian strains immunized chicken serum samples at 1:30 dilution, samples 11 and 12 were H5 subtype strains and samples 13-17 were non-H5 subtype strains. The results were expressed as the arithmetic mean of percent blocking value (n=5/group+S.E.)

DETAILED DESCRIPTION OF THE INVENTION

Figure 1A:
FIGS. 1A-1B. Characterization of mAb 5F8 by immunofluorescence assay (IFA) and Western blotting.

The present invention is directed to mAbs and related binding proteins that bind specifically to the HA1 protein of the H5 subtype of AIV and to the use of those mAbs and related binding proteins in epitope blocking ELISAs. The mAb tests positive against all known Indonesian strains of H5N1 AIV and other H5 subtypes by IFA and Western blot analysis.

In particular, one such mAb or related antigen-binding protein possesses the immunological binding characteristics of mAb 5F8 as produced by hybridoma 5F8, deposited with the American Type Culture Collection (ATCC), located at 10801 University Boulevard, Manassas, Va. 20110, USA, under the terms of the Budapest Treaty on Nov. 6, 2007, and assigned Accession Number PTA-8757. A second such mAb or related binding protein possesses the immunological binding characteristics of mAb 1G5 as produced by hybridoma 1G5, deposited with the ATCC on Nov. 6, 2007, and assigned accession number PTA-8756. The invention further relates to methods for the detection and diagnosis of H5 subtype AIV infection and assay kits that comprise the mAbs or binding proteins of the invention. The commonly available serological assays for influenza are HI, AGID and microneutralization assay, but as noted above, these tests have their drawbacks, and a sensitive and specific serological assay for the detection of human antibodies to AIV has been needed. Indirect ELISA for the detection of antibodies to influenza infection has been suggested as a sensitive method for the rapid screening of a large number of samples, but such an assay can require highly purified antigen and may exhibit cross-reactivity among HAs of different subtypes [18]. This invention further relates to highly sensitive and specific epitope blocking ELISAs (EB ELISA) for detecting H5 subtypes.

Various terms are used herein which have the following meanings:

The term Aimmunological binding characteristics@ of a mAb or related binding protein, in all of its grammatical forms, refers to the specificity, affinity and cross-reactivity of the mAb or binding protein for its antigen.

The term Abinding protein@ refers to a protein that includes the antigen binding site of a mAb of the present invention or a mAb having the immunological binding characteristics of a mAb of the present invention.

A monoclonal antibody having the binding characteristics of mAb 5F8 or mAb 1G5 is prepared by immunizing an animal with recombinant H5N1 HA0 protein. Such an antigen can be used as immunogen to generate antibodies with the desired immunological binding characteristics. Such antibodies include, but are not limited to, monoclonal antibodies, chimeric antibodies single chain antibodies, Fab fragments and proteins comprising the antigen binding sequence of mAb 5F8 or mAb 1G5.

MAb 5F8 has been found to recognize a specific epitope, comprising the amino acid sequence CNTKCQTP (SEQ ID NO:1), which has been shown to exist in all H5N1 strains found in humans and over 99% of all strains from all known sources, including chickens, identified to date. The epitope also is shown to be very stable (not subject to mutations). The epitope is highly antigenic, such that antibodies to the epitope are found in the serum of essentially any infected individual, which makes the epitope very reliable in a diagnostic test.

MAb 1 G5 has been found to recognize a specific epitope, comprising the sequence IHPLTIGE (SEQ ID NO:2), which has been shown to exist in all of the 1288H5N1 strains from all sources identified to date. This epitope also is very stable and highly antigenic, such that antibodies to the epitope are found in the serum of essentially any individual, thus making this epitope also very reliable in a diagnostic test.

A monoclonal antibody of this invention can be obtained by any technique that provides for the production of antibody molecules by continuous cell lines in culture. Such methods include, but are not limited to, the hybridoma technique originally developed by Kohler and Milstein (1975, *Nature* 256: 495-497), as well as the trioma technique, the human B-cell hybridoma technique (Kozbor et al., 1983, *Immunology Today* 4:72), and the EBV-hybridoma technique to produce human monoclonal antibodies (Cole et al., 1985, in *Monoclonal Antibodies and Cancer Therapy*, Alan R. Liss, Inc., pp. 77-96). Human antibodies can be used and can be obtained by using human hybridomas (Cote et al., 1983, *Proc. Nat=l. Acad. Sci. U.S.A.*, 80:2026-2030) or by transforming human B cells with EBV virus in vitro (Cole et al., 1985, in *Monoclonal Antibodies and Cancer Therapy*, Alan R. Liss, pp. 77-96). Moreover, techniques developed for the production of "chimeric antibodies" or "humanized antibodies" (Morrison et al., 1984, *J. Bacteriol.* 159-870; Neuberger et al., 1984, *Nature* 312:604-608; Takeda et al., 1985, *Nature* 314:452-454) by introducing sequences from a murine antibody molecule of the present invention, together with genes from a human antibody molecule of appropriate biological activity, can be used. Chimeric antibodies are those that contain a human Fc portion and a murine (or other non-human) Fv portion. Humanized antibodies are those in which the murine (or other non-human) complementarity determining regions (CDR) are incorporated into a human antibody. Both chimeric and humanized antibodies are monoclonal. Such human or humanized chimeric antibodies are preferred for use in in vivo diagnosis or therapy of human diseases or disorders.

An additional embodiment of the invention utilizes the techniques described for the construction of Fab expression libraries (Huse et al., 1989, *Science* 246: 1275-1281) to allow rapid and easy identification of monoclonal Fab fragments with the desired specificity for an antibody of the present invention, or its derivatives, or analogs.

Antibody fragments that contain the idiotype of the antibody molecule can be generated by known techniques. For examples, such fragments include, but are not limited to, the F(ab=)$_2$ fragment which can be produced by pepsin digestion of the antibody molecule; the Fab= fragments which can be generated by reducing the disulfide bridges of the F(ab=)$_2$ fragment, and the Fab fragments which can be generated by treating the antibody molecule with papain and a reducing agent. Such antibody fragments can be generated from any of the polyclonal or monoclonal antibodies of the invention.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), immunofluorescence assays and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Means are known in the art for detecting binding in an immunoassay and are within the scope of the present invention.

The 5F8 binding protein of the present invention, as discussed below, has been found to recognize an epitope of H5N1 HA having the amino acid sequence CNTKCQTP (SEQ ID NO:1). This epitope has been found to be highly conserved in all human and essentially all chicken influenza H5 subtypes, as well as in the great majority of influenza H5 subtype of other species of animals and birds. Specifically, of the 1288 influenza A H5N1 HA strains available in the NCBI Database, 99.61% (1283) contain the CNTKCQTP (SEQ ID NO:1) sequence. Of these 1288 strains, 280 are human H5N1 strains, and all of them contain this sequence. In addition, of 427 chicken H5N1 strains, all but one contain the CNTKCQTP (SEQ ID NO:1) sequence. In total, only 5 of the non-human H5 strains contained a variation of the CNTKCQTP (SEQ ID NO:1) sequence: 1H5 strain obtained from a duck had the sequence CNTRCQTP (SEQ ID NO:3), 1 strain obtained from a goose had the sequence CNTRCQTP (SEQ ID NO:3), and 2 strains obtained from chickens had the sequence CNTKCQTL (SEQ ID NO:4) or CNAKCQTP (SEQ ID NO:5). A total of 427 strains from chicken, 5 strains from herons, 189 strains from ducks and 62 strains from geese were tested. The epitope also was found to be highly conserved in such species as turkeys, mallards, pigeons, great barbets, green pea fowl, peacocks, tree sparrows, peregrine falcons, black-headed gulls, golden pheasants, eagle owls, partridges, whooper swans, ostriches, house crows, magpies, sparrows and mynas.

The 1G5 binding protein of the present invention, as discussed below, has been found to recognize an epitope of H5N1 HA having the amino acid sequence IHPLTIGE (SEQ ID NO:2). This epitope has been found to be highly conserved in all human influenza H5subtypes as well as in all influenza H5subtypes of other species known to date. The foregoing antibodies can be used in methods known in the art relating to the detection or localization of the H5 subtype of AIV, e.g. Western blotting, ELISA, radioimmunoassay, immunofluorescence assay, immunohistological assay, and the like. In addition, in a preferred embodiment, the antibodies can be used in an epitope blocking ELISA as discussed in more detail below. These assays provide for the qualitative and quantitative determination of the H5 subtype of AIV and for the diagnosis and surveillance of animals or humans infected with the virus.

The present invention also includes assay and test kits for the qualitative and/or quantitative detection of the H5 subtype of AIV. Such assay systems and test kits can comprise a labeled component prepared, e.g., by labeling the mAb or related binding protein of the present invention or a binding partner thereof. The assay or test kits further can comprise reagents, diluents and instructions for use, as is well known to those skilled in the immunoassay techniques.

In certain embodiments of the invention, such kits will contain at least the mAb or related binding protein of the invention, components for detecting immunospecific binding of the mAb or related binding protein to AIV in a biological sample, and instructions for use, depending upon the method selected, such as epitope blocking, competitive, sandwich, and the like. The kits also can contain positive and negative controls. They can be configured to be used with automated analyzers or automated immunohistochemical slide staining instruments.

An assay kit further can comprise a second antibody or binding protein that can be labeled or provided for attachment to a solid support (or attached to a solid support). Such an antibody or binding protein can be, for example, one which binds to AIV. Such second antibodies or binding proteins can be polyclonal or monoclonal antibodies.

A preferred kit is one to be used in an epitope blocking ELISA. Such a kit comprises a mAb or related binding protein which binds to epitope CNTKCQTP (SEQ ID NO:1) or to epitope IHPLTIGE (SEQ ID NO:2) of the HA1 envelope glycoprotein of an H5 subtype of AIV, the HA1 glycoprotein or a portion thereof comprising the amino acids of the epitope and reagents for detecting binding of said binding protein to said epitope.

Monoclonal antibodies to H5 subtype hemagglutination protein can be prepared by immunizing animals with AIV or H5 protein or fragments thereof. A preferred method involves amplification of the H5 subtype HA0 gene, followed by expression of the gene, recovery and purification of H5 recombinant proteins and use of the proteins as immunogens. For example, H5N1 AIV is propagated by inoculation of chicken embryos with available strains of the virus, followed by isolation of the viral RNA. The HA0 gene is amplified from cDNA, cloned into bacteria and then expressed. The proteins so produced can be used to immunize mice or other suitable species for production of hybridomas.

Hybridomas are screened for their ability to stably produce high affinity mAbs that are capable of specifically binding to H5 protein and distinguishing them from other AIV subtypes.

In accordance with this invention, one immunoglobulin mAb, a mAb determined to be of IgM isotype and designated 5F8, has been found to be strongly positive for Indonesian H5 subtypes strains known, as well as for other H5 strains, and to show no cross-reaction with any other subtypes tested, including H7N1, H3N2, H4N2 and H9N2.

In a second embodiment of this invention, another mAb, determined to be of isotype IGM and designated 1G5, also has been found to be strongly positive for Indonesian H5 subtype strains known, as well as for other H5 subtypes, and to show no cross-reaction with any other subtypes tested, including H7N1, H3N2, H4N2 and H9N2.

Both mAb 5F8 and 1G5 recognize linear epitopes of H5N1 hemagglutinin. The strength of mAb 5F8 is greater when the two antibodies are used at the same concentration. The separate linear epitopes recognized by the two antibodies increases the sensitivity for detecting the H5 antigen. The epitope recognized by mAb 5F8 is a universal epitope and, as discussed above, the eight amino acids of that epitope are present in all known human and almost all of the total 1288 known H5N1 influenza A sequences currently available in the gene bank. The 1G5 mAb recognizes an eight amino acid epitope present in all human influenza H5 subtypes as well as in all H5 subtype strains from other species currently known and available in the gene bank. The distance between the two epitopes (amino acids 290-297 and amino acids 310-317) allows for high affinity for antigen binding and detection.

This invention provides a convenient, highly specific and sensitive means for detecting H5 subtype AIV. One such means is an epitope blocking ELISA (EB ELISA). In an EB ELISA, specific antibodies from positive sera inhibit a selected mAb from recognizing its specific epitope such that color development is inhibited when a color-producing reagent which binds to the selected mAb is added to the sample. Negative sera, however, allow a strong color reaction. The assay depends on the ability of H5 influenza antibodies present in the biological sample to block binding of a selected H5 HA1 mAb to H5N1 influenza antigen or recombinant antigen adsorbed on a micro titer plate. More specifically, in an EB ELISA of this invention, ELISA plates are coated with an optimal concentration of recombinant HA1 or an inactivated H5N1 strain in a coating buffer. An optimal concentration can be determined by using a checkerboard titration by two dimensional serial dilution of coating antigen and a known positive antibody and selecting the most favorable concentration which gives maximal optical density (O.D.) value in the ELISA reading. Test sera samples are added to each well of the coated plates and incubated, washed and then incubated with mAb 5F8 or 1G5 supernatant. Plates are washed again and the bound mAb is detected by the addition of diluted horseradish peroxidase (HRP)-labeled antibody, such as an HRP-labeled rabbit anti-mouse antibody, which binds to the mAb 5F8 or 1G5. The plates are washed and then incubated with 3,3',5,5'-tetramethyl benzidine or other color-producing reagent, such as 2,2-Azino-bis(3-ethylbenzothiazoline-6-sulfonic acid or o-phenylenediamine dihydrochloride. The reaction is stopped and the color development read. The percent inhibition of the colorimetric reaction caused by antibodies in the sample which block the binding of the 5F8 or 1G5 mAb to the antigen is calculated for each serum sample.

The epitope blocking ELISA provides a convenient, highly specific and sensitive means for detecting H5 subtype AIV. This preferred detection method enables the detection of HA antigen from various H5 subtype strains of AIV without cross-reaction from other AIV subtypes. The EB ELISA can detect lower levels of antibody than can be consistently detected in other tests.

The strong reactivity of mAb 5F8 and mAb 1G5 also means that the antibodies can be used in antigen capture ELISAs (AC ELISAs) in which the antigen can be detected from live viruses or inactivated or lysed viruses in clinical samples. AC-ELISA can be a rapid, reliable and economical method for the detection of H5 antigen and can be used to detect H5HA antigens from both poultry and human isolates of H5N1.

The H5-subtype mAbs of this invention thus are highly advantageous diagnostic tools. As noted above, they are highly specific for the infectious H5N1 subtype AIV. This specificity has been verified in an assortment of H5N1-infected tissue specimens obtained from various sources. Such highly specific monoclonal antibodies represent a clear advantage for H5N1 diagnosis. The mAbs can be used in a safe and convenient diagnostic test for the detection of H5 AIV.

The following examples are provided to illustrate the present invention and are not to be construed as limiting.

EXAMPLE 1

I. Experimental

Viruses

Twenty four isolates of Indonesian H5N1 influenza strains used in this study and listed in Table 1 below (entries 1-24) were obtained from the National Institute of Health, Research and Development, Indonesia. Other H5 and non-H5 subtypes were provided by the Agri-Food and Veterinary Authority (AVA) of Singapore (entries 25-31 of Table 1).

TABLE 1

The avian influenza viruses used in this experiment

| Serial No. | Viruses | Subtypes |
|---|---|---|
| 1. | Human/Indonesia/CDC7/06* | H5N1 |
| 2. | Human/Indonesia/CDC326/06* | H5N1 |
| 3. | Human/Indonesia/CDC329/06* | H5N1 |
| 4. | Human/Indonesia/CDC370/06* | H5N1 |
| 5. | Human/Indonesia/CDC390/06* | H5N1 |
| 6. | Human/Indonesia/CDC523/06* | H5N1 |
| 7. | Human/Indonesia/CDC594/06* | H5N1 |
| 8. | Human/Indonesia/CDC595/06* | H5N1 |
| 9. | Human/Indonesia/CDC597/06* | H5N1 |
| 10. | Human/Indonesia/CDC610/06* | H5N1 |
| 11. | Human/Indonesia/CDC623/06* | H5N1 |
| 12. | Human/Indonesia/CDC644/06* | H5N1 |
| 13. | Human/Indonesia/CDC669/06* | H5N1 |
| 14. | Human/Indonesia/TLL01/06* | H5N1 |
| 15. | Human/Indonesia/TLL02/06* | H5N1 |
| 16. | Duck/Indonesia/TLL60/06* | H5N1 |
| 17. | Human/Indonesia/TLL177/06* | H5N1 |
| 18. | Human/Indonesia/TLL298/06* | H5N1 |
| 19. | Human/Indonesia/TLL485/06* | H5N1 |
| 20. | Human/Indonesia/TLL530/06* | H5N1 |
| 21. | Human/Indonesia/TLL540/06* | H5N1 |
| 22. | Human/Indonesia/TLL540/06* | H5N1 |
| 23. | Human/Indonesia/TLL561/06* | H5N1 |
| 24. | Human/Indonesia/TLL565/06* | H5N1 |
| 25. | Duck/Singapore/Singapore/97 | H5N3 |
| 26. | Chicken/Singapore/Singapore/98 | H5N2 |
| 27. | Chicken/Singapore/Singapore/92 | H4N1 |
| 28. | Chicken/Singapore/Singapore/02 | H3N2 |
| 29. | Common Iora/Indonesia/F89/11/95 | H7N1 |
| 30. | Chicken/Singapore/Singapore/98 | H9N2 |
| 31. | Mandarin Duck/Singapore/Singapore/93 | H10N5 |

*Highly pathogenic AIV

Both high pathogenic and low pathogenic viruses were inoculated in the allantoic cavity of 11 day old embryonated chicken eggs. The allantoic fluid was harvested from the eggs after 48 hours incubation. Virus titers were determined using Hemagglutination assays. The virus then was clarified and stored at −80EC. All experiments with live viruses were performed in a biosafety level 3 containment laboratory and all the animal experiments were carried out in an Animal biosafety level 3 (ABSL3) containment laboratory in compliance with CDC/NIH and WHO recommendations [12,13] and also were approved by the Agri-Food and Veterinary Agency (AVA) and Ministry of Health (MOH) of Singapore.

Molecular Cloning

H5N1 (CDC/669/Indonesia/06) was inactivated with beta-propiolactone [14] and total RNA was extracted using Trizol (Invitrogen, Carlsbad, Calif., USA). The HA0 gene was amplified from the cDNA and cloned into pQE-30 vector (Qiagen, Germany) using standard cloning techniques for expression in bacteria. The clones were transformed into *Escherichia coli* M15 pREP4 competent cells to express the protein. The HA1 gene from the same strain was cloned into pFASTBAC-HT, a vector used to construct a recombinant baculovirus harboring the H5N1 HA1 gene (Invitrogen, Carlsbad, Calif.) which then was used to infect Sf-9 cells propagated in Sf-900 II medium for the development of an immunofluorescent assay to screen for H5 HA1-specific mAbs.

Production of Recombinant H5N1 HA0 Protein (rHA0)

The transformed *E. coli* M15 cells were grown at 37EC to an $OD_{600}$ of 0.5-0.6 in Luria-Bertani (LB) medium containing ampicillin (100 μg/ml) and protein expression was induced by the addition of 1 mmol/L IPTG for 3 hours with shaking. Cells were pelleted and resuspended in phosphate buffered saline (PBS). The histidine fusion protein was purified on Ni-NTA column (Quiagen, Germany) and the protein was used for analysis by SDS-PAGE and Western blot.

Production of Monoclonal Antibodies

Four adult female BALB/c mice, 4-6 weeks old, were immunized intramuscularly three times with 25 μg of recombinant H5N1 HA0 protein in 0.1 ml of PBS, which was emulsified with an equal volume of adjuvant (SEPPIC, France). Mouse humoral immune responses were monitored with IFA and indirect enzyme linked immunosorbent assay (ELISA).

Three days before the fusion, the mice were boosted intravenously with 25 μg of recombinant H5N1 HA0 protein in 0.1 ml of PBS and spleen cells were harvested and fused with SP2/0 cells as described previously [15]. The fused cells were seeded in 96-well plates and their supernatants were screened by immunofluorescence assay using mock-infected or recombinant baculovirus-infected Sf9 cells, H5N2- and H5N3-infected MDCK cells as antigen as described below. Hybridomas in positive wells were cloned two times by limiting dilution. Positive clones were checked for isotype by using a one-minute isotyping kit (Amersham Bioscience, England) as described in the manufacturer=s protocol. The hybridoma cultures were harvested and cell debris was removed by centrifugation at 400×g for 10 minutes. The supernatant was collected and stored at −20EC.

Immunofluorescence Assay (IFA)

Sf-9 and MDCK cells in 96-well plates were infected with either recombinant baculovirus harboring the truncated H5N1 HA1 gene or AIV H5N1 Indonesian strains, H5N2 and H5N3 strains, respectively. At 36 hours (for Sf-9 cells) and 24-48 hours (for MDCK cells) post-infection, the cells were fixed with 4% para-formaldehyde for 30 minutes at room temperature and washed three times with PBS, pH 7.4. The fixed cells were incubated with hybridoma culture fluid at 37EC for 1 hour. Cells were rinsed three times with PBS and incubated with a 1:40 dilution of fluorescein isothiocyanate (FITS)-conjugated rabbit anti-mouse Ig (Dako, Denmark). Cells were rinsed again in PBS prior to scoring results in an epifluorescence microscope (Olympus, Japan) with appropriate barrier and excitation filters for optimized FITC visualization.

One immunoglobulin, IgM MAb, designated 5F8, was strongly positive for all Indonesian strains. It was selected for epitope mapping and further development of the blocking ELISA.

Immunoblotting

The selected mAb 5F8 was evaluated by immunoblotting assays. The recombinant H5N1 HA0 protein and whole purified H5N1 Indonesian strains and H5N2 and H5N3 strains were fractionated on 12% SDS-PAGE under non-reducing conditions. The separated proteins were electro-transferred and immobilized onto nitrocellulose membrane. The membrane was blocked with 5% non-fat milk in PBS containing 0.1% Tween-20 (PBST) at 37EC for 1 hour. The membrane subsequently was incubated with hybridoma supernatant, rinsed in PBST and incubated with HRP-conjugated rabbit anti-mouse Ig. The membrane bound antibody was detected with rabbit anti-mouse conjugated to HRP. The membrane was developed by incubation with ECL reagents (Amersham Biosciences) [16].

Epitope Mapping of 5F8

To locate the epitope of 5F8, the rHA1 protein was dissected into five overlapping fragments (See FIG. 2A). The corresponding fragments of DNA were PCR amplified using gene specific primers and clones into pQE-30 vector (Qiagen, Germany). The clones were transformed into *E. coli* M15pREP4 competent cells (Qiagen, Germany) to express histidine fusion proteins. The transformed *E. coli* M15 cells were grown at 37EC to an $OD_{600}$ of 0.5-0.6 in Luria-Bertani (LB) medium containing ampicillin (100 μg/ml) and protein expression was induced by the addition of 1 mmol/L IPTG for 3 hours with shaking. Cells were pelleted and resuspended in phosphate buffered saline (PBS). The expressed fusion-peptides were used for epitope mapping by Western Blot.

For the second step of the epitope mapping, eight further truncated peptides were expressed which were an extension of fragment four but truncated in the fragment five region (FIG. 2B). These eight sub-fragments also were expressed as histidine-fusion (His-fusion) peptides as described above and were used for Western blot analysis. For the final step, 14 mutants were generated having point mutations to mutate amino acids 287-300. All of the amino acids were mutated to alanine except the Ala-297, which was mutated to glycine in a series of mutants. The point mutants were generated using a PCR-based site-directed mutagenesis protocol.

These mutants also were expressed as His-fusion peptides as described above, and Western blot was carried out to exactly determine the amino acids forming the epitope for mAb 5F8.

Testing of Sera

To determine the specificity of the epitope-blocking ELISA using selected mAb 5F8, human and chicken serum samples were tested and the results were compared with those of HI assay. The samples used for the present study were divided into human and chicken groups. The human group consisted of 25 human sera samples divided into three groups. Group 1 comprised 10 serum samples originating from H5N1 influenza infected and recovered patients and obtained from the Ministry of Health (MOH), Indonesia. The infection was confirmed by PCR and certified by the MOH, Indonesia. Group 2 consisted of 5 healthy volunteers vaccinated with commercial influenza virus vaccine (FLUARIX7) within the previous six months. FLUARIX7 contains hemagglutinin (HA) of each of the following three virus strains: A/Solomon Islands/3/2006 (H1N1), A/Wisconsin/67/2005 (H3N2) and B/Malaysia/2506/2004. Group 3 consisted of 10 healthy volunteers known to have no history of influenza infection and no use of an influenza vaccine. All samples were certified for their status by the MOH, Indonesia.

Positive sera were generated using groups of chickens (n=5) from non-vaccinated healthy flock. Chickens were inoculated intramuscularly with all 24 inactivated Indonesian H5N1 strains (Table 1) and non-H5 subtypes, such as H3N2, H4N1, H7N1 and H9N2, were emulsified in ISA-70 (SEPPIC, France) adjuvant twice at two week intervals. Sera samples were collected on the $10^{th}$ day after each of the $1^{st}$ and $2^{nd}$ immunizations and were evaluated for antibodies against appropriate strains by IFA and indirect ELISA as described above. Other positive sera were obtained from chick experimentally infected with low pathogenic H5N2 or H5N3 two weeks after virus challenge.

Epitope-blocking ELISA

Optimal concentrations of H5N1 viral antigen/recombinant HA1 and 5F8 mAb were determined by checkerboard titration to provide near-maximal binding of 5F8 mAb. U-bottomed 96-well ELISA plates were coated with highly purified, optimal concentration of recombinant HA1 or CDC/523H5N1 inactivated viral strain at 100 μL/well under appropriate biological containment and incubated overnight at 4EC in coating buffer (0.1 mol/L carbonate/bicarbonate, pH 9.6). Antigen-coated plates were washed three times with PBS-T (phosphate-buffered saline [ph 7.5] containing 0.05% Tween 20) and non-specific sites were blocked with 100 μL blocking buffer (PBS containing 5% skim milk) for 1 hour at 37EC. Test sera samples were serially diluted twofold in PBS-T, and 100 μL were added to each well and incubated for 45 minutes at 37EC. The plates were washed four times with PBS-T and incubated with 100 μL of MAb supernatant for 1 hour at 37 EC. Plates again were washed four times and the bound MAb was detected by the addition of 100 μL of peroxidase-labeled rabbit anti-mouse Ig diluted 1:1000, incubated for 1 hour at 37EC. After washing with PBS-T, the plates were incubated with 100 μL of 3, 3', 5, 5'-tetramethyl benzidine (Sigma, USA). The reaction was stopped by adding 0.1N sulfuric acid and the color development was read at 450 nm. The percent inhibition of the colorimetric reaction caused by sample antibodies, blocking the binding of the MAb to the antigen was calculated for each serum at different dilutions by using the formula for percent inhibition as follows:

Percentage of inhibition=100−[OD (test serum)/OD (negative control)×100]. A threshold of 50% inhibition by the test serum was considered >positive= for H5HA antibodies. Results were expressed as percent inhibition of MAb binding, relative to the inhibition caused by the test sample.

II. Results

Characterization of Monoclonal Antibodies

Figure 1B:
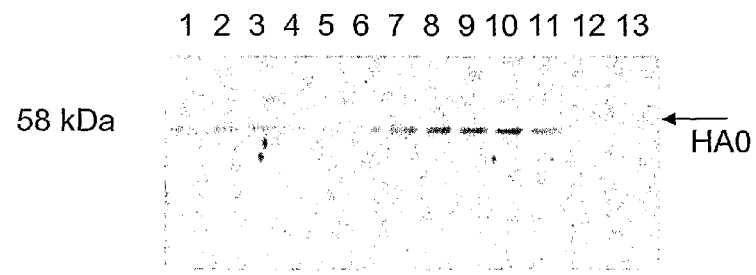

A panel of hybridoma clones secreting mAbs to H5HA1 antigen was screened by immunofluorescence (IFA) against all 24 Indonesian H5N1 influenza strains and other H5 and non-H5 subtypes. The results showed that 5F8 MAb strongly reacted with all MDCK cells infected with all H5 subtypes and Sf-9 cells infected with baculovirus expressing recombinant HA1 and yielded positive cytoplasmic immunofluorescence patterns (FIGS. 1A-1 and 1A-3), which were identical to those obtained with rabbit anti-H5N1 serum. All the other subtypes, such as H7N1, H3N2, H4N2 and H9N2-infected MDCK cells did not give a fluorescence signal (FIGS. 1A-2 and 1A-4). The mAb 5F8 was screened for the ability to detect native HA1 of H5N1 strains or H5 subtypes and rHA1 by Western blotting (FIG. 1B). The mAb 5F8 strongly reacted with all Indonesian H5N1 strains and H5 subtypes and no cross-reaction was observed with any other subtypes such as H7N1, H3N2, H4N2 and H9N2, by Western blotting. Based upon the sensitivity and specificity of the monoclonal antibody by IFA and Western blot, 5F8 mAb was selected for epitope mapping and then for use in EB-ELISA. The isotype of 5F8 mAb was determined as IgM class.

Epitope Mapping of mAb

In the first step of epitope mapping, Western blot results showed that mAb 5F8 reacted with fragment 5 (amino acids 256 to 337) (FIGS. 2A and 2B; in FIG. 2B, the first "C" stands for control and "A B C D E" stand for the name of the fragment as mentioned in FIG. 2A).

For the second step of epitope mapping, truncated peptides were expressed which were an extension of fragment four but truncated in the fragment five region (represented by the diagram in FIG. 2A). These eight subfragments also were expressed as histidine-fusion peptides as described above and were used for Western blot analysis (FIG. 2C). Western blot results showed that mAb 5F8 reacted with fragments 8, 7, 6, 5 and 4, indicating that the epitope is within region 287 to 300. In the third and final step, each of amino acids 287 to 300 in the fourth fragment was mutated to alanine and the protein was expressed in *E. coli* as a histidine-fusion protein. Western blot results showed positive results with mutants Y287A, G288A, N289A, M298A, Ga99A and A300G. The mutants C290A, N291A, T292A, K293A, C294A, Q295A, T296A and P297A showed negative results on the Western blot. These data indicate that the mutants of the amino acids which showed negative results are the one which are involved in the epitope and so, upon being mutated, were not recognized by mAb 5F8. The other mutants were recognized by the mAb in spite of the mutations, indicating that they are not involved in forming the epitope. These data indicate that the specific amino acids involved in the epitope were CNTKCQTP (SEQ ID NO:1).

Epitope Blocking ELISA

The diagnostic efficacy of an epitope blocking ELISA assay was characterized by its ability to detect H5HA antibodies in human and chicken serum samples. All recovered human sera samples from H5N1 influenza infection tested positive in epitope-blocking ELISA performed with mAb 5F8 with mean blocking values of >50% at a dilution of >96 depending upon the recovered time from the infection (Table 3B). The HI test also showed the HI titer of 24 (log $2^4$-$2^5$). Samples with non-H5 vaccinated human sera showed 10-15% inhibition at 1:5 dilution. However, hemagglutination inhibition assay showed the HI titer of 14.4 (log $2^3$-$2^8$), indicating cross-reactivity. The normal human sera showed <7% blocking of the MAb binding to its antigenic site.

All the H5N1 immunized chicken serum samples tested positive in epitope-blocking ELISA performed with mAb 5F8 with mean blocking values of >50% at a mean serum dilution of >47 (40-57.6) on day 10 after the first immunization. Day 10 after the second immunization showed mean serum dilution of >296.46 (256-328) blocking the mAb binding to its corresponding epitope. However, the hemagglutination inhibition assay showed the HI titer log $2^3$-$2^4$ and log $2^8$ $2^9$ on those days (Day 7 and 14). The non-H5 subtypes infected sera samples showed maximum blocking of 15% to 20% at 1:2 to 1:4 dilutions. Among the non-H5 subtypes tested, however, H3N2 immunized sera showed positive (log $2^4$) in HI test on peak day 10 after the second immunization (Table 3a).

Figures 3A, 3B:
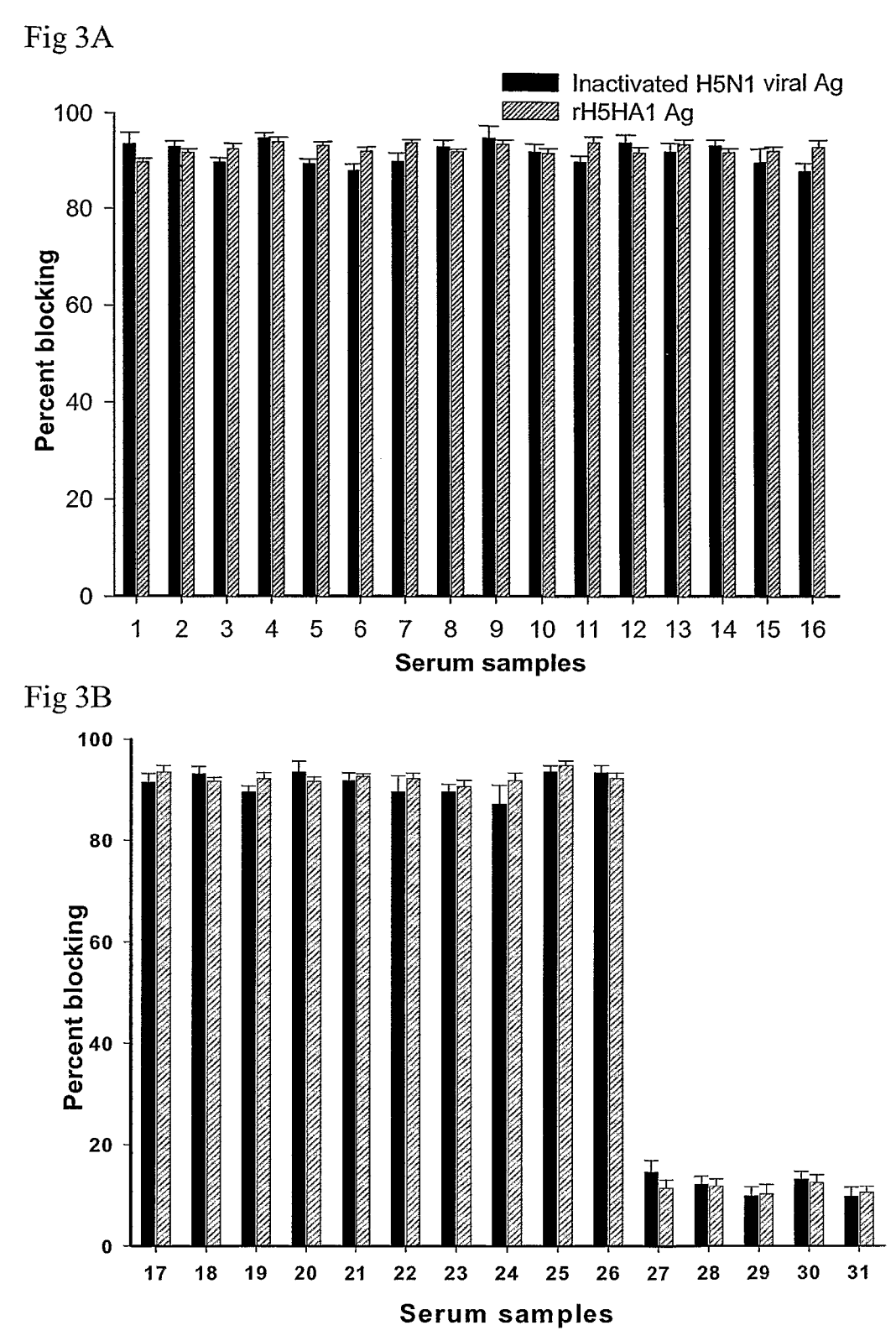

Moreover, as shown in FIGS. 3A and 3B, the antibody responses showed similar kinetics in using both rH5HA and H5N1 viral antigen for blocking. This study provides demonstration of recombinant H5HA antigen as alternative H5N1 viral antigens for blocking ELISA for the detection of antibodies.

TABLE 2

| Lane | Mutant No. | 287 | 288 | 289 | 290 | 291 | 292 | 293 | 294 | 295 | 296 | 297 | 298 | 299 | 300 | WB |
|---|---|---|---|---|---|---|---|---|---|---|---|---|---|---|---|---|
| 1 | Wildtype | Y | G | N | C | N | T | K | C | Q | T | P | M | G | A | + |
| 2 | Y287A | A | G | N | C | N | T | K | C | Q | T | P | M | G | A | + |
| 3 | G288A | Y | A | N | C | N | T | K | C | Q | T | P | M | G | A | + |
| 4 | N289A | Y | G | A | C | N | T | K | C | Q | T | P | M | G | A | + |
| 5 | C290A | Y | G | N | A | N | T | K | C | Q | T | P | M | G | A | − |
| 6 | N291A | Y | G | N | C | A | T | K | C | Q | T | P | M | G | A | − |
| 7 | T292A | Y | G | N | C | N | A | K | C | Q | T | P | M | G | A | − |
| 8 | K293A | Y | G | N | C | N | T | A | C | Q | T | P | M | G | A | − |
| 9 | C294A | Y | G | N | C | N | T | K | A | Q | T | P | M | G | A | − |
| 10 | Q295A | Y | G | N | C | N | T | K | C | A | T | P | M | G | A | − |
| 11 | T296A | Y | G | N | C | N | T | K | C | Q | A | P | M | G | A | − |
| 12 | P297A | Y | G | N | C | N | T | K | C | Q | T | A | M | G | A | − |
| 13 | M298A | Y | G | N | C | N | T | K | C | Q | T | P | A | G | A | + |
| 14 | G299A | Y | G | N | C | N | T | K | C | Q | T | P | M | A | A | + |
| 15 | A300G | Y | G | N | C | N | T | K | C | Q | T | P | M | G | G | + |

TABLE 3a

| Chicken serum antibody against viral Strain | H1 log 2 titer against CDC523 H5N1 strain | | Serum titer[a] at 50% blocking the 5F8 mAb binding to the CDC523 H5HA1 epitope (Blocking ELISA) | |
|---|---|---|---|---|
| | Day 10 after 1st Immunization | Day 10 after 1st Immunization | Day 10 after 1st Immunization | Day 10 after 2nd Immunization |
| H5N1/IndonesisCD7/06 | 3.6±0.48 | 7.8±0.40 | 42.0±3.22 | 304±9.79 |
| H5N1/Indonesia/CDC326/06 | 3.2±0.40 | 7.8±0.40 | 43.2±4.08 | 296±9.79 |
| H5N1/Indonesia/CDC329/06 | 3.4±0.48 | 7.2±0.40 | 42.0±5.11 | 288±8.01 |
| H5N1/Indonesia/CDC370/06 | 4.2±0.40 | 7.2±0.40 | 43.6±4.98 | 304±9.79 |
| H5N1/Indonesia/CDC390/06 | 3.6±0.48 | 7.8±0.40 | 44.8±7.83 | 304±9.79 |
| H5N1/Indonesia/CDC523/06 | 4.4±0.40 | 8.6±0.48 | 57.6±4.66 | 328±19.53 |
| H5N1/Indonesia/CDC594/06 | 3.6±.48 | 7.6±0.48 | 40.0±4.38 | 304±9.79 |
| H5N1/Indonesia/CDC595/06 | 3.6±0.40 | 8.2±0.40 | 51.2±5.42 | 312±8.01 |
| H5N1/Indonesia/CDC597/06 | 4.2±0.40 | 7.8±0.54 | 44.8±6.49 | 272±8.01 |
| H5N1/Indonesia/CDC610/06 | 3.8±0.48 | 7.6±0.48 | 43.6±4.40 | 264±9.79 |
| H5N1/Indonesia/CDC623/06 | 3.6±0.48 | 8.0±0.52 | 42.4±5.11 | 304±9.97 |
| H5N1/Indonesia/CDC644/06 | 3.8±0.40 | 8.2±0.40 | 41.6±4.87 | 320±21.90 |
| H5N1/Indonesia/CDC699/06 | 4.2±0.48 | 8.2±0.40 | 44.8±3.20 | 304±9.79 |
| H5N1/Indonesia/TLL01/06 | 4.2±0.40 | 8.2±0.40 | 48.8±2.65 | 312±8.01 |
| H5N1/Indonesia/TLL02/06 | 3.8±0.48 | 7.8±0.40 | 46.4±2.99 | 264±9.79 |
| H5N1/Indonesia/TLL60/06 | 3.6±0.48 | 7.6±0.48 | 45.6±3.48 | 272±9.79 |
| H5N1/Indonesia/TLL177/06 | 4.2±0.48 | 7.6±0.48 | 41.2±3.07 | 256±9.79 |
| H5N1/Indonesia/TLL298/06 | 3.8±0.40 | 7.6±0.48 | 47.2±2.65 | 264±8.01 |
| H5N1/Indonesia/TLL485/06 | 4.2±0.40 | 7.6±0.48 | 46.4±2.99 | 272±9.79 |
| H5N1/Indonesia/TLL530/06 | 3.8±0.48 | 8.4±0.48 | 54.4±2.99 | 320±21.90 |
| H5N1/Indonesia/TLL535/06 | 3.8±0.48 | 8.2±0.40 | 51.2±3.20 | 288±8.01 |
| H5N1/Indonesia/TLL540/06 | 3.6±0.40 | 8.2±0.48 | 56.0±2.52 | 296±9.79 |
| H5N1/Indonesia/TLL561/06 | 4.2±0.40 | 7.6±0.48 | 49.6±2.99 | 288±8.01 |
| H5N1/Indonesia/TLL565/06 | 4.2±0.40 | 8.2±0.40 | 46.4±2.99 | 296±9.79 |
| H5N2/Singapore/98 | 3.6±0.48 | 8.4±0.48 | 57.6±2.99 | 304±9.79 |
| H5N3/Singapore/97 | 4.2±0.40 | 8.4±0.48 | 51.2±1.95 | 328±19.59 |
| H3N2/Singapore/02 | 2.4±0.50 | 4.2±0.40 | — | — |
| H4N1/Singapore/92 | — | — | — | — |
| H7N1/Singapore/94 | — | — | — | — |
| H9N2/Singapore/98 | — | — | — | — |
| H10N5/Singapore/93 | — | — | — | — |

[a] Serum titer at 50% blocking the mAb binding was expressed each individual chicken serum was blotted and was found mean values and expressed (n = 5/group ± S.E.)

TABLE 3B

| Human serum samples | H1 titer against H5N1 strain | Serum titer[a] at 50% blocking the mAb binding |
|---|---|---|
| H5N1 infected sera (n = 10) | 24.0±2.67 | >96±13.50 |
| Non-H5 vaccinated sera | 14.6±1.6 | 0.0±0.0 |

[a] Serum titer at 50% blocking the mAb binding was expressed each individual human serum was blotted and was found mean values and expressed (mean value/group ± S.E.)

The results of the EB-ELISA and the HI test, commonly used for serological testing for antibodies to influenza infection, illustrate the capacity of the EB-ELISA in comparison to existing serological tests. The results of the testing with 10 well-defined positive human H5N1 sera samples and 15 well-defined negative sera samples, including 5 sera from non-H5 vaccinated donors, demonstrate the reliability of the EB-ELISA, which is able to identify all anti-H5N1 positive sera and does not cross-react with non-H5 vaccinated sera. When serially diluted serum samples were tested in both the EB ELISA and the HI test, the ELISA was able to detect lower antibody levels than the HI and did not cross-react with non-H5 vaccinated sera samples. The HI test, in contrast, reacted with heterologous anti-HA antibodies of non-H5 vaccinated sera samples.

The sensitivity of the EB ELISA also was determined by testing chicken sera samples from well-defined positive samples from 24H5N1 Indonesian strains, as well as H5N2 and H5N3 strains. Again, the results showed that the blocking test detects lower antibody levels than the HI test and also tested for specificity. The EB ELISA did not cross-react with serial dilutions of heterologous anti-HA antibodies of non-H5 subtypes. In the HI test, however, cross-reactivity was observed with H3HA antibody, and the mean HI titer was found to be log $2^{2.4}$, log $2^{4.2}$ on day 10 after the first and second immunizations, respectively. Comparison of antibody titers determined by the EB ELISA and HI revealed that the former is superior in sensitivity and specificity when examining both human and chicken sera. Although the HI test is effective and sensitive, it requires hazardous virus production and handling, which is a significant limitation to its desirability. Recombinant H5HA antigen, in contrast, can be prepared in any laboratory with cell culture facilities, since the antigen is not infectious and does not represent a hazard to susceptible animals.

Detection of antibodies to avian influenza viruses in mammalian species, including humans, using HI assays generally have failed, even in cases in which experimental infection was confirmed by virus isolation [25]. Furthermore, HAs of the H1, H2, H3, H5, and H6 subtypes have been shown to contain a cross-reactive epitope recognized by anti-HA antibody [26, 27]. The EB-ELISA developed in this study was highly specific for influenza H5 subtypes. It can be used for large scale sero-epidemiological studies to determine the mode of transmission of the virus and the risk factors associated with influenza H5 infection in human beings, animals and birds.

The CNTKCQTP (SEQ ID NO:1) sequence of the epitope recognized by mAb 5F8 (aa 290-297) has been found to be highly conserved in all human and essentially all chicken influenza H5 subtypes. It also is conserved in almost all H5 subtype strains from other species of animals and birds. The region is not present in any of the non-H5 hemagglutinins except H1 subtypes and has been found in the latter only in mutated form. The 5F8 mAb thus is particularly useful because the stability and high immunogenicity of the epitope makes the antibody very specific for diagnosing H5 subtypes.

EXAMPLE 2

I. Experimental

A second monoclonal antibody, designated 1G5, was generated following the general procedures of Example 1 to obtain hybridoma supernatant. The mAb was raised against the recombinant HA0 protein, cloned from H5N1 influenza virus strain A/goose/Guangdong/97.

Immunofluorescence Assay (IFA)

Sf-9 and MDCK cells were seeded in 960 well plates and incubated with recombinant baculovirus harboring truncated H5N1 HA1 gene and H5N1 viruses, respectively. At 36 hours post-infection, the cells were fixed with 4% paraformaldehyde for 30 minutes at room temperature. All washes were performed with PBS, pH 7.4. Fixed cells were incubated with hybridoma culture fluid at 37° C. for 1 hour, washed and incubated with a 1:50 dilution of fluorescein isothiocyanate (FITC)-conjugated rabbit anti-mouse Ig. Cells were washed and fluorescence was visualized using an Olympus IX71 microscope with appropriate barrier and excitation filters.

One mAb, designated 1G5, determined to be an IgM mAb, tested positive against all 24 known Indonesian strains, as well as against other H5 subtypes by IFA and Western blot analyses. It was selected for epitope mapping and further development of the blocking ELISA.

Immunoblotting

Immunoblotting was carried out in accordance with the general procedures of Example 1.

Epitope Mapping of 1G5

The epitope for mAb 1G5 was mapped using a fragmented protein over-expression protocol. To locate the epitope of 1G5, the rHA1 protein was dissected into five overlapping fragments, as shown in FIG. 5A, using the protocol set forth in Example 1.

For the second step of the epitope mapping, eight further truncated peptides were expressed which were an extension of fragment four but truncated in the fragment five region. These eight sub-fragments also were expressed as histidine-fusion peptides as described in Example 1. For the final step, 13 mutants were generated having point mutations to mutate amino acids 308-320. All of the amino acids were mutated to alanine in a series of mutants. The point mutations were generated using a PCR-based site-directed mutagenesis protocol. The mutants also were expressed as His-fusion peptides as described in Example 1, and Western blot analysis was carried out to determine exactly the amino acids forming the epitope for mAb 1G5.

Testing of Sera

The specificity of the epitope-blocking ELISA using mAb 1G5 was determined in accordance with the procedures set forth in Example 1.

Epitope-blocking ELISA

MAb 1G5 was used in an epitope blocking ELISA in accordance with the teachings of Example 1.

II. Results

Characterization of Monoclonal Antibody

Figures 4A, 4B:
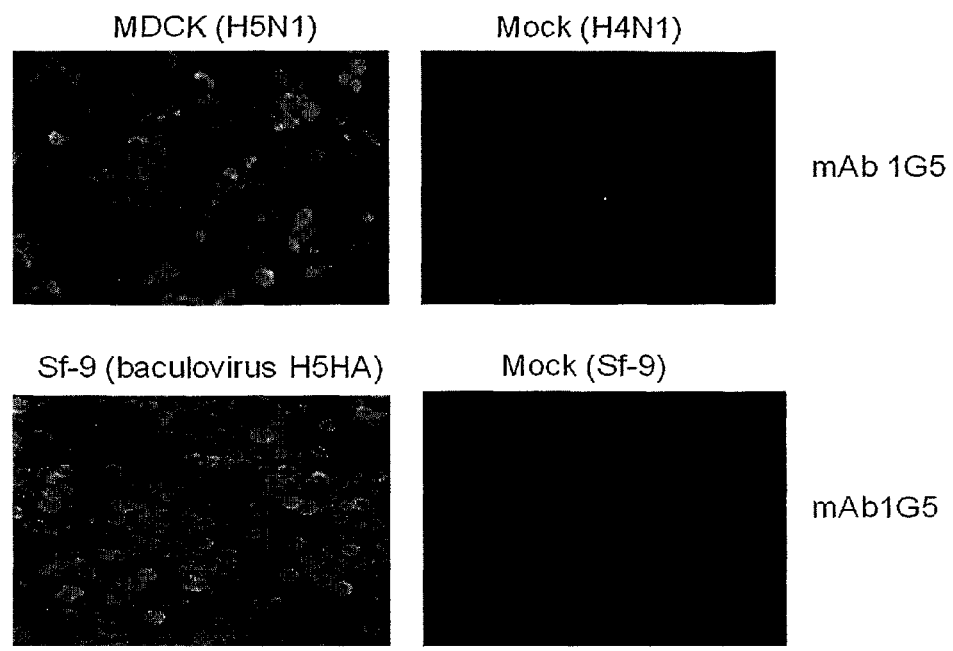
FIGS. 4A-4B. Characterization of mAb 1G5 by immunofluorescence assay (IFA) and Western blotting.

A panel of hybridoma clones secreting mAbs to H5A1 antigen was screened by immunofluorescence (IFA) against all 24 known Indonesian H5N1 influenza strains and other H5 and non-H5 subtypes. The results showed that mAb 1G5 strongly reacted with all MDCK cells infected with all H5 subtypes and Sf-9 cells infected with baculovirus expressing recombinant HA1 and yielded positive cytoplasmic immunofluorescence patterns (FIGS. 4A-1 and 4A-3) identical to those obtained with rabbit anti-H5N1 serum. All the other subtypes, such as H7N1 (FIGS. 4A-2 and 4A-4), H3N2, H4N1, H9N2 and H10N5, did not give a fluorescent signal. The mAb 1G5 was screened for the ability to detect native HA1 of H5N1 strains or H5 subtypes and rHA1 by Western blotting (FIG. 4B). MAb 1G5 strongly reacted with all known Indonesian H5N1 strains and H5 subtypes; no cross-reaction was observed with the other subtypes by Western blotting. Based upon the sensitivity and specificity of the monoclonal antibody by IFA and Western blot, 1G5 mAb was selected for epitope mapping and then for use in EB-ELISA. The isotype of mAb 1G5 was determined to be of class IgM.

Epitope Mapping of mAb 1G5

Figure 5B:

In the first step of epitope mapping, Western blot analysis of the fragments showed that mAb 1G5 reacted with the fifth fragment, between amino acids 256 and 337 (FIG. 5B).

TABLE 4

Results of Western blotting

| | Amino acid number | Results on Western blot-1G5 |
|---|---|---|
| rHA1 | 1-337 | + |
| Fragment A | 1-75 | − |
| Fragment B | 61-135 | − |

TABLE 4-continued

Results of Western blotting

| | Amino acid number | Results on Western blot-1G5 |
|---|---|---|
| Fragment C | 121-195 | − |
| Fragment D | 181-255 | − |
| Fragment E | 241-337 | + |

To further map the epitope, in the second step, 8 sub-fragments of the 5$^{th}$ fragment were expressed as extensions of the fourth fragment and expressed as His-fusion proteins. Western blot results (FIG. 5C) showed that 1G5 reacted with fragments 6, 7 and 8, indicating the epitope to be in the region of amino acids 308 to 320.

TABLE 5

Results of Western blotting

| | Amino acid no: | Result on Western blot |
|---|---|---|
| Sub-fragment 1 | 256-270 | − |
| Sub-fragment 2 | 256-280 | − |
| Sub-fragment 3 | 256-290 | − |
| Sub-fragment 4 | 256-300 | − |
| Sub-fragment 5 | 256-310 | − |
| Sub-fragment 6 | 256-320 | + |
| Sub-fragment 7 | 256-330 | + |
| Sub-fragment 8 | 256-337 | + |

These results indicated that the epitope is present in the region between amino acids 308 and 320. The tentative epitope for 1G5 was determined to be HNIHPLTIGECPK (SEQ ID NO:6).

Figure 5C:
Figure 5D:
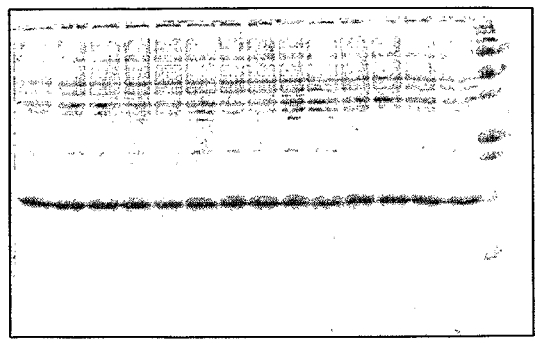
Figure 5D:
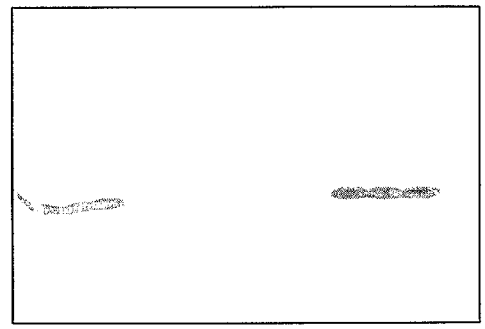

In the third step, point mutations were introduced into the clone SF6, such that all the amino acids from 308 to 320 were mutated to alanine, one amino acid at a time, and the protein fragments were expressed again as His-fusion proteins. It was observed that the mAb did not react with the protein fragments mutated in amino acids 310 to 317 but showed positive reactions with the others on a Western blot (FIG. 5C). From these results, it was concluded that the epitope recognized by mAb 1G5 is IHPLTIGE (SEQ ID NO:2).

TABLE 6

Western blot analysis of the point mutated fragments

| Lane number | Mutant | Result of Western Blot |
|---|---|---|
| 1 | Wildtype | + |
| 2 | H308A | + |
| 3 | N309A | + |
| 4 | I310A | − |
| 5 | H311A | − |
| 6 | P312A | − |
| 7 | L313A | − |
| 8 | T314A | − |
| 9 | I315A | − |
| 10 | G316A | − |
| 11 | E317A | − |
| 12 | C318A | + |
| 13 | P319A | + |
| 14 | K320A | − |
| 15 | Protein marker | − |

The IHPLTIGE (SEQ ID NO:2) sequence of the epitope recognized by mAb 1G5 has been found to be highly conserved in all human and chicken influenza subtypes identified to date. The region is not present in any of the non-H5 hemagglutinins except certain H1 subtypes in which the epitope region contains mutations and is non-reactive with the antibody. The 1G5 mAb thus is highly useful because the stability and high immunogenicity of the epitope makes the antibody very specific for diagnosing H5 subtypes.

Epitope Blocking ELISA

Figure 8:
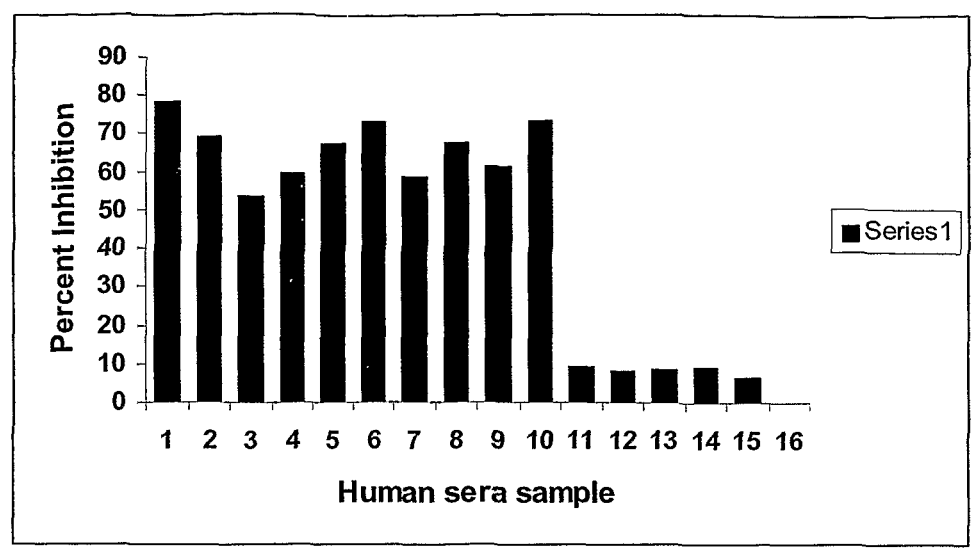
FIG. 8 shows 50% blocking of mAb 1G5, relative to the CDC/523H5HA1 epitope caused by human sera from infected and vaccinated samples (samples 1-10: infected and recovered serum samples; samples 11-15: vaccinated human serum samples; sample 16: healthy human control serum)
Figure 9A:
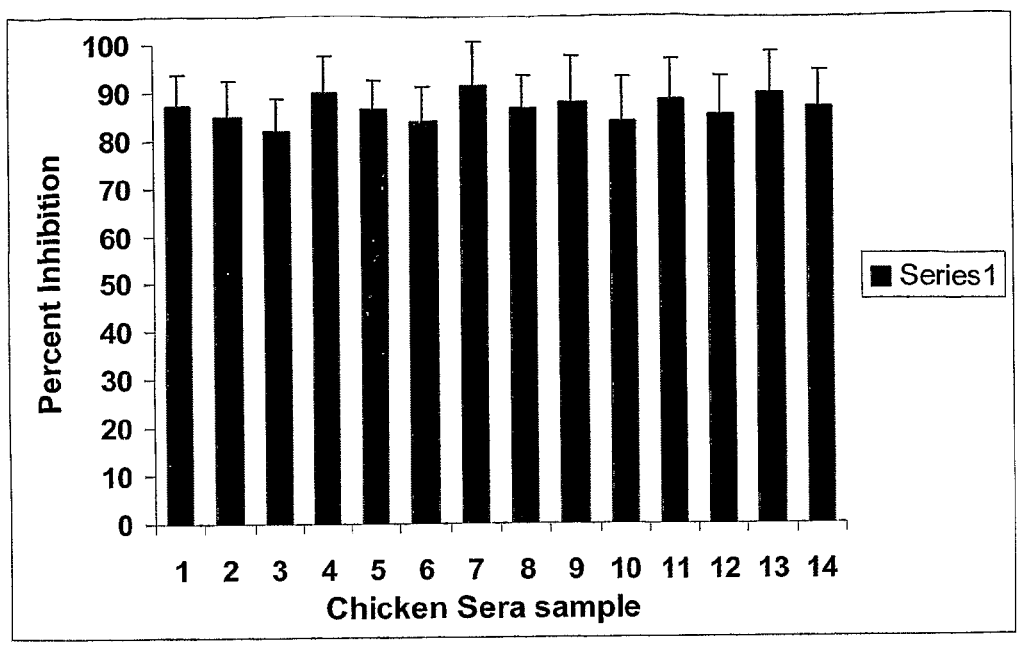
FIGS. 9A and 9B show 50% blocking of mAb 1G5 binding relative to the CDC/523H5HA1 epitope caused by immunized chicken sera.
Figure 9B:
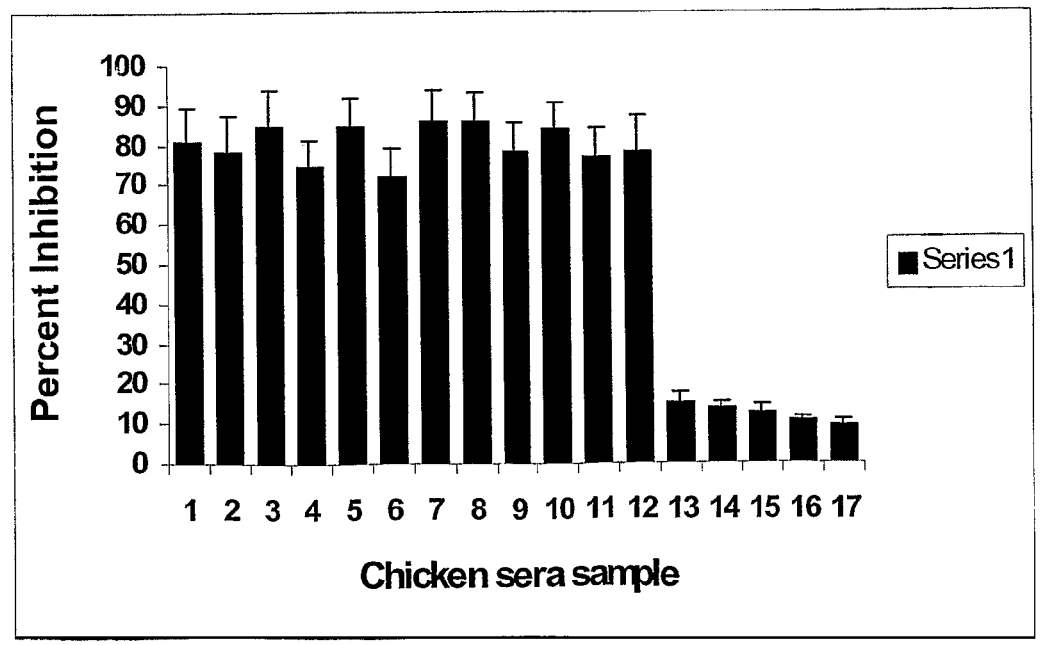

The diagnostic efficacy of epitope blocking ELISA assay was characterized by its ability to detect H5HA antibodies in human and chicken serum samples. All the H5N1 immunized human and chicken serum samples tested positive in EB-ELISA performed with mAb 1G5 with mean blocking values of 50% at a mean serum dilution of 1:30 in chickens (See FIG. 8 and FIGS. 9A and 9B) and 1:10 dilution in recovered human serum samples (FIG. 8). Moreover, samples with non-H5 vaccinated human sera showed 7-13% inhibition at 1:5 dilutions. In contrast, HI assay showed the HI titer log$2^2$.

EXAMPLE 3

Development of Antigen Capture ELISA (AC-ELISA)

96-well plates (Nunc, Denmark) were coated with purified mAbs 5F8 and/or 1G5 in 50 µl carbonate buffer (73 mM sodium bicarbonate and 30 mM sodium carbonate) and incubated at 37° C. for 1 hour or at 4° C. overnight. After each incubation step, the plates were washed 3 times with PBS containing 0.05% Tween 20 (PBST), and all dilutions were made in PBST containing 1% non-fat milk. The plates were blocked by incubation with 100 µl of blocking solution (5% non-fat milk in PBS-T at 37° C. for 1 hour, rinsed and incubated with 50 µl of purified highly pathogenic H5N1 Indonesian strains/low pathogenic AIV H5 subtypes (H5N1/PR8, H5N2 and H5N3)/other non-H5 subtypes at 37° C. for 1 hour. After rinsing, 100 µl of guinea pig monospecific antibody IgG (1:500 dilution) were added, incubated for 1 hour at 37° C., washed and further incubated with 100 µl of HRP-conjugated rabbit anti-guinea pig immunoglobulin (diluted 1:1000). Color development was performed by the addition of 100 µl TMB substrate solution; reactions were stopped by the addition of 4M $H_2SO_4$ and A450 values measured using a sunrise Tecan Remote ELISA plate reader. Working concentrations of mAbs and monospecific antibodies were determined by checkerboard titration.

Figure 6A:
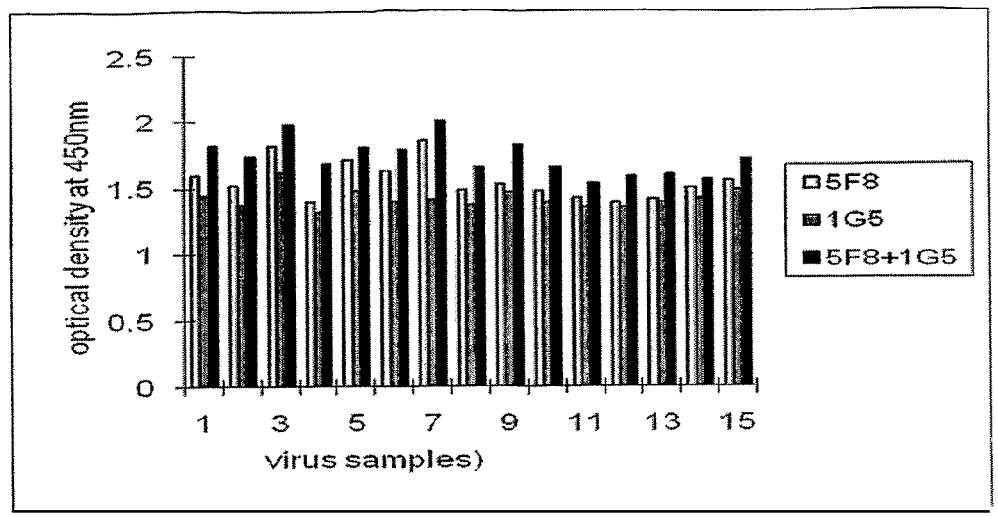
FIGS. 6A and 6B illustrate that mAbs 5F8 and 1G5 specifically react with H5 subtype.
Figure 6:
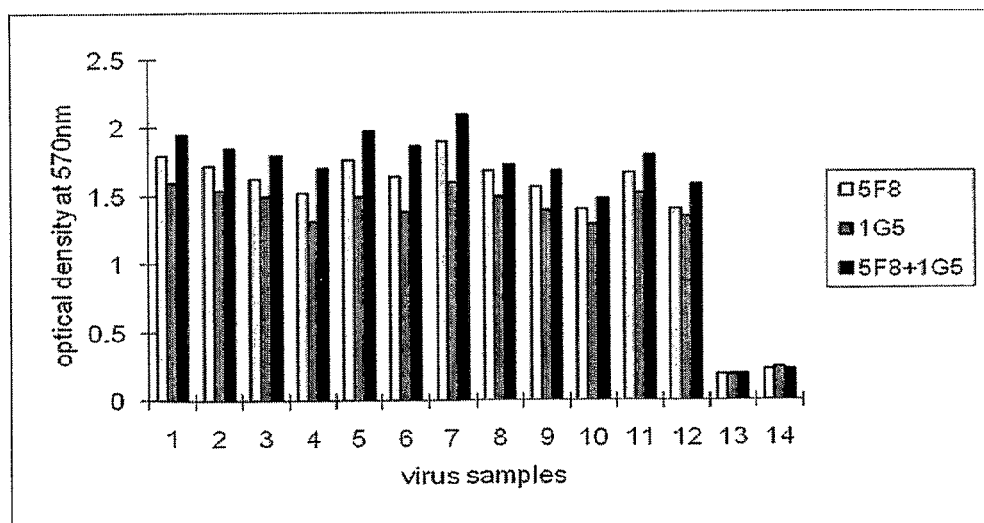
Figure 7:
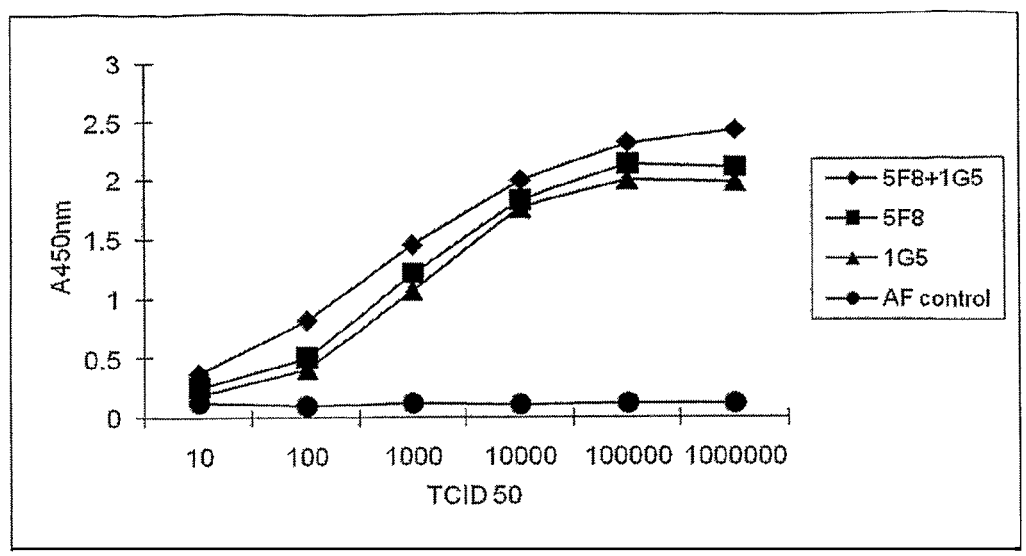
FIG. 7 shows that both mAb 5F8- and mAb 1G5-based antigen capture ELISAs detected $10^2$ TCID50 units of H5N1. An H4N1-containing assay did not yield absorbances significantly above background levels.

In order to optimize the AC-ELISA, monoclonal and polyclonal antibodies were used interchangeably as capture and detection antibodies. When the microtiter plate coated with guinea pig anti-rHA1 polyclonal antibody, a much lower absorbance was recorded compared to that recorded when the plate coated with mAbs as the capture antibody. Therefore, mAbs were used as the capture antibody, while polyclonal antibody served as the detector antibody. The combination of mAb 5F8 and mAb 1G5 used as capture antibodies gave stronger detection signals than either of the mAbs alone (FIGS. 6A and 6B). Combination of the two monoclonal antibodies shows high affinity and specificity for detecting H5 antigen in AC-ELISA. No cross-reaction with any other subtype was observed. Assays based on both mAb 5F8 and mAb 1G5 detected $10^2$ TCID$_{50}$ units of H5N1 (FIG. 7). An H4N1-containing assay did not yield absorbances significantly above background levels.

Mapping the two mAbs showed that they are directed to two different epitopes of the same HA1 antigen. Their separate linear epitopes increase the sensitivity for the detection of the H5 antigen. The epitope recognized by mAb 5F8 is a universal-epitope and the eight amino acids of the epitope are present in almost all of the available 1288 influenza a H5N1 sequences in the gene bank. The epitope recognized by mAb 1G5 is present in all 1288 influenza H5 subtype strains presently known and available in the gene bank. The distance between the two epitopes creates a high affinity for antigen binding and detection.

References

1. World Health Organization (WHO). H5N1 Avian influenza: Timeline of major events. 2007. Available at http://www.whoint/csr/disease/avian_influenza/timeline_28_10a.pdf. Accessed 20 Sep. 2007.
2. World Health Organization (WHO). H5N1 Avian influenza: Timeline of major events. 2007. Available at http://www.whoint/csr/disease/avian_influenza/timeline2007_06_21pdf. Accessed 18 Sep. 2007.
3. World Health Organization (WHO). Cumulative Number of Confirmed Human Cases of Avian Influenza A/(H5N1) Reported to WHO 10 Sep. 2007. Available at: http://ww.who.int/csr/disease/avian_influenza/country/cases_table_2007_09_10/en/index.html. Accessed 20 Sep. 2007.
4. World Health Organization (WHO). Avian influenza-situation in Indonesia-update 16. Available at http://www.who.int/csr/don/2007_09_10/en/index.html. Accessed 20 Sep. 2007.
5. Mounier-Jack S, Coker R J. How prepared is Europe for pandemic influenza? Analysis of national plans. Lancet 2006; 367:1405-11.
6. Sedyaningsih E R, Isfandari S, Setiawaty V, et al. Epidemiology of cases of H5N1 virus infection in Indonesia, July 2005-June 2006. J Infect Dis 2007; 196:522-7.
7. Petric M, Comanor L, Petti C A. Role of the laboratory in diagnosis of influenza during seasonable epidemics and potential pandemics. J. Infect Dis 2006; 194: S98-110.
8. Julkunen I, Phyala R, Hovi T. Enzyme immunoassay, complement fixation and hemagglutination inhibition tests in the diagnosis of influenza A and B virus infections: purified hemagglutinin in subtype specific diagnosis. J Virol Methods 1985; 10:75-84.
9. Massicot J, Murphy B R. Comparison of the hemagglutination-inhibiting and neutralizing antibody responses of volunteers given 400 chick cell-agglutinating units of influenza A/New Jersey/76 split-virus vaccine. J Infect Dis 1977; 136:S472-4.
10. de Jong M D, Hien T T. Avian influenza A (H5N1)-Review. Clin Virol 2006; 35: 2-13.
11. Blitvich, B. J., Marlenee N L, Hall R A et al. Epitope-blocking enzyme linked immunosorbent assays for the detection of serum antibodies to west nile virus in multiple avian species. J. Clin Microbiol 2003; 41:1041-7.
12. Centers for Disease Control and Prevention (U.S.), an National Institutes of Health (U.S.) 1999. Biosafety in microbiological and biomedical laboratories, 4th ed. U.S. Dept. of Health and Human Services Public Health Service Centers for Disease Control and Prevent; National Institutes of Health; For sale by the Supt. of Docs. U.S. G.P.O., Washington [Bethesda, Md.] Washington, D.C.
13. World Health Organization. 2004. Laboratory biosafety manual, 3rd ed. World Health Organization, Geneva.
14. Goldstein M A, Tauraso N M. Effect of formalin, beta-propiolactone, merthiolate, and ultraviolet light upon influenza virus infectivity chicken cell agglutination, hemagglutination, and antigenicity. Appl Microbiol 1970; 19:290-4.
15. Yokoyama W M. 2001. Production of monoclonal antibody. p.p. 2.5.1-2.5.17. In: Coligan J. E., A. M. Kruisbeek, D. H. Marguilies, E. M. Shevach, W. Strober (eds.). Current protocols in immunology. John Wiley & Sons, Inc., Newcastle, United Kingdom.
16. Gallgher S, Winston S E, Fuller S A, Hurrell J G R. 2004. Immunoblotting and immunodetection. In: Current Protocols in Molecular Biology (10.8.1-10.8.24). Eds by Ausubel F M, Brent R, Kinston R E, Moore D D, Seidman J G, Smith J A, Struhl K. John Wiley & Sons, Inc. Newcastle, United Kingdom.
17. Rowe T, Abernathy R A, Hu-Primmer J et al. Detection of antibody to avian influenza A (H5N1) virus in human serum by using a combination of serologic assays. J. Clin Microbiol 1999; 37: 937-41.
18. Burlington D B, Wright P F, van Wyke K L, Phelan M A, Mayner R E, Murphy B R. Development of subtype-specific and heterospecific antibodies to the influenza A virus hemagglutinin after primary infection in children. J. Clin Microbiol 1985; 21: 847-9.
19. de Boer F, Back W, Osterhaus A D M E. An ELISA for detection of antibodies against influenza. A nucleoprotein in human an various animal species. Arch. Virol. 1990; 115:47-61.
20. Singh B K, Ahuja S, Gulati B R. Developmental of monoclonal antibody-based blocking ELISA for detection of Equine Herpusvirus 1 antibodies. Vet Res Comm 2004; 28: 437-46.
21. Gut-Winiarska M, Jacobs L, Kerstens H, Bienkowaska-Szewczyk K. A highly specific and sensitive sandwich blocking ELISA based on baculovirus expressed pseudorabis virus glycoprotein B. 2000. J Virol Methods 2000; 88: 63-71.
22. Kuck D, Kern A, Kleinschmidt J A. Developmental of AAV serotype-specific ELISAs using novel monoclonal antibodies. J Virol Methods 2007; 140: 17-24.
23. Ameri-Mahabadi M, Zhou E, Hsu W H. Comparison of two swine Mycoplasma hyopneumoniae enzyme-linked immunosorbent assays for detection for antibodies from vaccinated pigs and field serum samples. J Vet Diagn Invest 2005; 17: 61-64.
24. Fevereiro M, Barros S, Fagulha T. Development of a monoclonal antibody blocking-ELISA for detection of antibodies against Maedi-Visna virus. J Virol Methods 1999; 81:101-108.
25. Profeta M L, Palladino G. Serological evidence of human infections with avian influenza viruses. Arch Virol. 1986; 90:355-60.
26. Okuno Y, Isegawa Y, Sasao F, Ueda S. A common neutralizing epitope conserved between the hemagglutins of influenza A virus H1 and H2 strains. J Virol 1993: 67: 2552-2558.
27. Govorkova E A, Smirnov Y A. Cross-protection of mice immunized with different influenza A (H2) strains and challenged with viruses of the same HA subtype. Acta Virol 1997: 41; 251-257.

The invention claimed is:

1. An antibody that binds specifically to an epitope of hemagglutinin of an H5 subtype of avian influenza virus and that has the immunological binding characteristics of monoclonal antibody 5F8 as produced by hybridoma 5F8 which is deposited with the American Type Culture Collection with Accession Number PTA-8757, wherein said immunological binding characteristics comprise binding to an epitope that is bound by monoclonal antibody 5F8.

2. The antibody of claim 1, which is a monoclonal antibody, a single chain antibody, an antibody fragment, a chimeric antibody or a humanized antibody.

3. The antibody of claim 1 which is a monoclonal antibody.

4. Monoclonal antibody 5F8 as produced by hybridoma 5F8 which is deposited with the American Type Culture Collection with Accession Number PTA-8757.

5. An antibody which binds to epitope CNTKCQTP (SEQ ID NO:1) of H5 hemagglutinin.

6. The antibody of claim 5 which is a monoclonal antibody, a single chain antibody, an antibody fragment, a chimeric antibody or a humanized antibody.

7. The antibody of claim 6 which is a monoclonal antibody.

8. A method of detecting H5 subtype avian influenza virus in a biological specimen which comprises
 (i) contacting the specimen
  (a) with an antigen which comprises an epitope of the envelope glycoprotein of an H5 subtype of avian influenza virus comprising sequence CNTKCQTP (SEQ ID NO:1) and
  (b) with an antibody that binds specifically to said epitope and that has the immunological binding characteristics of monoclonal antibody 5F8 as produced by hybridoma 5F8 which is deposited with the American Type Culture Collection with Accession Number PTA-8757, wherein said immunological binding characteristics comprise binding to said epitope that is bound by monoclonal antibody 5F8 and (ii) determining whether an antibody in the specimen binds to said epitope by determining how much of said antibody having the characteristics of mAb 5F8 binds to said antigen.

9. The method of claim 8, wherein said antibody is a monoclonal antibody.

10. The method of claim 9, wherein the monoclonal antibody is antibody 5F8 as produced by hybridoma 5F8, deposited with the American Type Culture Collection under Accession Number PTA-8757.

11. A kit for detecting H5 subtype avian influenza virus in a biological specimen which comprises an antibody that binds to epitope CNTKCQTP (SEQ ID NO:1) of the envelope glycoprotein of an H5 subtype of avian influenza virus, the glycoprotein or a portion thereof comprising the amino acids of said epitope and reagents for detecting binding of said antibody to said epitope, wherein said antibody binds specifically to said epitope and has the immunological binding characteristics of monoclonal antibody 5F8 as produced by hybridoma 5F8 which is deposited with the American Type Culture Collection with Accession Number PTA-8757, wherein said immunological binding characteristics comprise binding to said epitope that is bound by monoclonal antibody 5F8.

12. The kit of claim 11 wherein said antibody is a monoclonal antibody.

13. The kit of claim 11, wherein said reagents can detect whether said antibody is blocked from binding to said glycoprotein by the presence in said biological specimen of an antibody which recognizes said epitope of said glycoprotein.

14. The kit of claim 12, wherein the monoclonal antibody is antibody 5F8 as produced by hybridoma 5F8, deposited with the American Type Culture Collection under Accession Number PTA-8757.

15. The kit of claim 13, wherein the antibody is monoclonal antibody 5F8 as produced by hybridoma 5F8, deposited with the American Type Culture Collection under Accession Number PTA-8757.

* * * * *

UNITED STATES PATENT AND TRADEMARK OFFICE
CERTIFICATE OF CORRECTION

PATENT NO.        : 8,574,830 B2
APPLICATION NO. : 12/865543
DATED             : November 5, 2013
INVENTOR(S)       : Mookkan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 478 days.

Signed and Sealed this
Twenty-second Day of September, 2015

Michelle K. Lee
*Director of the United States Patent and Trademark Office*